United States Patent [19]

Falardeau

[11] Patent Number: 4,543,127
[45] Date of Patent: Sep. 24, 1985

[54] ORGANOTIN-FUMED SILICA DERIVATIVES FOR USE AS BIOCIDAL COMPOSITIONS

[75] Inventor: Edward R. Falardeau, Midland, Mich.

[73] Assignee: The Dow Chemical Company, Midland, Mich.

[21] Appl. No.: 607,377

[22] Filed: May 7, 1984

[51] Int. Cl.$^4$ .......................... A01N 9/00; C08K 5/54; C08K 5/57; C09D 5/14
[52] U.S. Cl. .................. 106/18.29; 106/15.05; 514/493; 514/63; 514/10; 514/84; 524/399; 523/122
[58] Field of Search .......................... 106/15.05, 18.29; 523/122; 424/184, 288; 260/429.7; 524/399

[56] References Cited

U.S. PATENT DOCUMENTS

| | | | |
|---|---|---|---|
| 3,445,249 | 5/1969 | Leebrick | 424/288 |
| 3,854,960 | 12/1974 | Plum et al. | 106/18.31 |
| 3,901,930 | 8/1975 | Wirth et al. | 523/122 |
| 4,010,276 | 3/1977 | Gitlitz | 424/288 |
| 4,115,130 | 9/1978 | Grump et al. | 106/18.28 |
| 4,157,999 | 6/1979 | Matsuda et al. | 106/15.05 |
| 4,221,839 | 9/1980 | De Graaf | 106/15.05 |
| 4,354,873 | 10/1982 | Supcoe et al. | 424/288 |

FOREIGN PATENT DOCUMENTS 1062324  3/1967  United Kingdom ............. 106/15.05

*Primary Examiner*—Allan M. Lieberman
*Attorney, Agent, or Firm*—D. L. Conneglio

[57] ABSTRACT

A biocidal composition is formed from an organotin compound covalently bonded to reactive silanol sites present on the surface of a silica compound to form a solid biocidal particle. Further, the solid biocidal particle can be admixed with a carrier or film-forming vehicle. A method of protecting a surface from fouling organisms is also provided by coating the surface with the subject biocidal composition while it is dispersed in a carrier or film-forming vehicle.

11 Claims, No Drawings

ORGANOTIN-FUMED SILICA DERIVATIVES FOR USE AS BIOCIDAL COMPOSITIONS

BACKGROUND OF THE INVENTION

The subject invention is generally directed toward a biocidal composition of an organotin compound covalently bonded to a silica compound to control the activity of the organotin compound. Further, a method for protecting a surface from foulants is disclosed through the use of the subject biocidal composition.

The use of organotin compounds of the general formula:

$$R_3SnX$$

wherein R is a lower hydrocarbyl group and X is an anionic radical such as oxide, sulphide, halide and organic acid radicals have long been recognized in the art as being an excellent biocidal compound effective against marine growth. Generally organotin compounds are incorporated into a coating composition which can be applied to the hull of a ship or any other surface which will be in contact with the water. The coating then releases the biocidal compound into the water to prevent marine growth. Naturally as the biocidal compound diffuses to the coating's surface and is released the effectiveness of the biocidal activity will decrease with time. Therefore, one goal has been to control the rate of biocidal release to prolong the effective life of the coating composition.

One method directed toward the slow, steady release of the biocidal compounds is attempted in U.S. Pat. No. 4,115,130. There the particular biocidal compound is entrapped in the internal porous structure of silica. While this method is said to slow down the escape of biocidal compounds there still remains room for improvement.

Another method disclosed in U.S. Pat. No. 3,854,960 attempts to retain a triorganotin compound in paints by admixing it with colloidal silicic acid obtained by the flame hydrolysis of silicon tetrachloride, i.e., fumed silica, or montmorillonite modified with quaternary ammonium salts. The advantage is disclosed as being due to the presence of silicon or montmorillonite in the paint and less on an adsorptive binding of the tributyltinoxide.

Despite the many methods known it is still desirable to control the biological activity of organotin compounds to better utilize them as antifoulants. Further, it is desirable to have a compound which can be dispersed in a carrier or coating vehicle of choice without regard to further modification of the particular vehicle.

SUMMARY OF THE INVENTION

In one aspect the present invention is a biocidal composition comprising an organotin compound covalently bonded to reactive silanol sites present on the surface of a silica compound to form a solid biocidal particle. The biocidal composition can additionally include a carrier or film-forming vehicle which contains the solid biocidal particle. The carrier vehicle may be a volatile or inert liquid and the film-forming vehicle may be wax, paint, varnish, or an adhesive composition. The preferred organotin compound is tributyltinoxide and the preferred silica compound is fumed silica.

In another aspect, the present invention is a method for protecting a surface from fouling organisms which comprises admixing, in a carrier or film-forming vehicle, a solid biocidal particle to form an admixture wherein the solid biocidal particle comprises an organotin compound covalently bonded to reactive silanol sites present on the surface of a silica compound, and treating the surface with the admixture. The carrier vehicle may be a volatile or inert liquid and the film-forming vehicle may be wax, paint, varnish or an adhesive composition. The preferred organotin compound is tributyltinoxide and the preferred silica compound is fumed silica.

Among the advantages of the subject invention are improved biocidal activity and versatility in application with various coating treatments for surfaces to be protected from fouling.

DETAILED DESCRIPTION OF THE INVENTION

A process for preparing a biocidal composition comprising an organotin compound covalently bonded to a silica compound is provided. These compositions exhibit biocidal activity such that they can be employed as marine antifoulants or, in the case of a tricyclohexyl derivative, as a miticide.

The process and product so formed requires organotin compounds which are well known in the art to be effective anti-fouling agents. Additionally, a silica compound to which the organotin compound can be covalently bonded is required.

Generally, the term "organotin compound", as used herein, is meant to include those compounds characterized by the structural formula $R_3SnX$ wherein R is an alkyl or aryl functionality and X is an anionic radical such as a halogen, sulphide, oxide, $OSnR'_3$, where R' is an alkyl or aryl group, or an organic acid radical. Preferably, the organotin compound is tri-n-butyltinmethoxide, tributyltinoxide, tri-n-butyltinchloride, tri-n-butyltinacetate, triphenyltinhydroxide, tributyltinhydride, tricyclohexyltin bromide, triphenyltinchloride and the like. Other suitable organotin compounds with anti-foulant activity can also be advantageously employed.

The term "silica compound", as used herein, is meant to include those compounds which contain reactive silanol sites. Reactive silanol sites describe hydroxyl groups present on the surface of the silica compounds. A broad range of potential silica compounds containing hydroxyl groups can be employed. The group of silica compounds known as fumed silica are excellent choices. This is due to the very abundant reactive silanol sites or hydroxyl groups present. For example, one type of commercially available fumed silica is Cab-O-Sil ® M-5 which has approximately 1.3 mmol SiOH/g $SiO_2$. Cab-O-Sil ® M-5 is a trademark of the Cabot Corporation. More generally, fumed silica can be prepared by methods known in the art such as by the flame hydrolysis of silicon tetrachloride.

The biocidal composition of the present invention is generally prepared by reacting a dried silica compound with an organotin compound under conditions sufficient to form a covalent bond between the organotin compound and the silica compound. The conditions necessary to react the components vary depending on the particular organotin compound employed. For example, tri-n-butyltinmethoxide reacts well at ambient temperatures while tri-n-butyltinoxide reacts better at an elevated temperature, i.e., 155° C. The proper reaction conditions can be determined by monitoring the silanol sites present on the silica compound.

Generally, the reaction of the organotin compound with the silica compound is monitored by infrared spectroscopy (IR) for the disappearance of the free OH bond of the silica compound in the IR spectra. The absence of the free OH bond in the IR spectra indicates the production of covalently bonded —OSnR$_3$ groups to the silica surface.

The proportion of reactants to be employed is generally limited by the number of free silanol sites available on the silica compound. The reactant ratio is preferably calculated such that all the organotin compound is covalently bonded to the surface of the silica compound. For the Cab-O-Sil ® M-5 fumed silica the number of available silanol sites is approximately 1.3 mmol Si-OH/g SiO$_2$. Therefore, in a typical preparation of the invention 1.3 mmol of organotin compound is employed for each gram of Cab-O-Sil ® M-5 fumed silica. The preferred ratio of free silanol sites to organotin active sites is 1:1.

The organotin compound, when covalently bonded to the silica compound, provides extended antifoulant life. It is believed that the chemical bonding of the silica and organotin compounds controls, slows and/or modifies the biological activity of the organotin to provide excellent resistance to marine organisms. In the case of tricyclohexyl derivatives, the product of the invention can be useful as a miticide. Further, the biocidal composition has the advantage of being dispersible in a coating of choice due to the solid particle formed by covalently bonding the organotin moiety to the fumed silica.

Generally, the biocidal composition of the invention is present as a fine white powder similar in appearance to underivatized fumed silica. The powder can be added to a carrier or film-forming vehicle which can then be applied to a surface to be protected. Various application methods well known in the art such as brush or spray painting, submersion, etc. can be employed to treat the surface to be protected with the subject biocidal composition. Carrier vehicles which are volatile or inert to the biocidal composition can be employed to leave a protective film of the biocidal composition on the surface. Typical film-forming vehicles are wax, paint, varnish and adhesives. Other suitable vehicles which can adhere to the substrate to be protected and accept the composition of the invention as either a filler or an ingredient are acceptable.

Coatings which contain the biocidal composition of the invention are excellent for protecting substrates from the growth of organisms, especially marine-type organisms. In particular, coatings containing the dispersed solid, biocidal particles may be used for treating materials such as textiles, wood, plastic, metal and the like upon which organisms would be expected to attach or upon which organisms may grow. This would especially include those surfaces exposed to sea water.

The marine anti-fouling characteristic of the subject biocidal composition was tested in an accelerated anti-fouling activity test conducted by Miami Marine Testing. The general procedure followed by Miami Marine Testing comprised mixing a 1 g sample of the potential antifoulant with 9 g of PVA-acrylic latex and pouring the mixture into a template to dry. The resulting films were then exposed to the ocean. Due to the thickening effect of the fumed silica a slight modification was made in that 4.129 g of water was first added to 2.161 g of PVA-acrylic latex followed by the addition of 0.216 g antifoulant of the subject invention. The slightly viscous mixture was then stirred and 15 mil films were cast on panels.

The testing was conducted by immersing the panels 2.54 cm in the ocean water near Miami. The test duration was the time required for a blank latex coated standard panel to become completely fouled. In addition to the blank standard panel a 2.5 percent tributyltinoxide loaded latex and a 10 percent tributyltinoxide loaded latex were included for comparison. The 10 percent tributyltinoxide panel was the normal standard employed by Miami Marine Testing and the 2.5 percent tributyltinoxide panel was included because this level represented the approximate active biocide level of the panels prepared by the invention. Results of the testing are shown below.

| | | Fouling Resistance | | |
| --- | --- | --- | --- | --- |
| | | Weight Percent Organotin | Anti-foulant Rating[1] | |
| Sample | Anti-fouling Material | in Latex | Topside | Underside |
| 1* | Blank[2] | — | 0 | 0 |
| 2* | (Bu$_3$Sn)$_2$O | 10.00 | 10 | 9 |
| 3* | (Bu$_3$Sn)$_2$O | 2.50 | 9 | 3 |
| 4+ | (SiO$_2$)$_{12.9}$OSnBu$_3$ | 2.72 | 9 | 8 |
| 5++ | (SiO$_2$)$_{12.6}$OSnBu$_3$ | 2.77 | 10 | 9 |

*Not an example of the invention.
+Prepared as in Example 2.
++Prepared as in Example 1.
[1]Each anti-foulant sample was rated separately for algae (topside) and animal forms (underside) on a scale from 0 to 10. A rating of 0 indicates entire surface area was fouled while 10 indicates no macrofoulants attached.
[2]Panel coated with plain latex resin.

As is indicated by the results, Samples 4 and 5 of the invention showed excellent results as compared to the comparison Samples 1–3. The very good underside ratings for Samples 4 and 5 show that the activity of the biocide was as good as a much higher level of potential active biocide as contained by Sample 2. Further, Samples 4 and 5 showed better overall activity than the approximately equal biocide level of Sample 3. Thus, indicating the advantage of the subject invention.

The preparation of the present invention is illustrated below by way of examples.

EXAMPLE I

A 19.1 g sample of Cab-O-Sil ® M-5 fumed silica was dried by heating to 350° C. for 1.25 hours in a 1 liter resin pot with stirring under nitrogen. To the dehydrated fumed silica was added 3.0 ml of tri-n-butyltinmethoxide ((C$_4$H$_9$)$_3$SnOCH$_3$) dropwise with a syringe over several minutes at 23° C. The materials were allowed to mix for 1 hour. An additional 2.1 ml aliquot of tri-n-butyltinmethoxide was added dropwise with a syringe and the mixture was stirred for an additional hour. Finally, 1.6 ml of tri-n-butyltinmethoxide was similarly added and allowed to stir 3 hours. A total of 6.7 ml or 25 mmol of tri-n-butyltinmethoxide were added over the course of 5 hours to 19.1 g or 318 mmol of fumed silica. IR analysis showed the disappearance of the free silanol band which indicated loss of the silanol group from the silica surface and formation of the covalent bond between the silica and tri-n-butyltinmethoxide. The product stoichiometry was (SiO$_2$)$_{12.6}$[OSn(C$_4$H$_9$)$_3$] and was present as a fine white powder.

EXAMPLE II

A 16.7 g sample of Cab-O-Sil ® M-5 fumed silica was dried as in Example I and 3.5 g of tri-n-butyltinoxide ($[(C_4H_9)_3Sn]_2O$) was added and stirred for 3 hours at 23° C. An additional 3.5 g of tri-n-butyltinoxide was added and the temperature of the mixture was raised to 155° C. for one hour. In total 7.0 g or 11.8 mmol of tri-n-butyltinoxide was added to 16.7 g or 278 mmol of fumed silica. A fine white powder of the tri-n-butyltin/-silica product was collected.

EXAMPLE III

The same procedure as employed in Example I was followed to prepare a product of tri-n-butyltinchloride and fumed silica. A 19.6 g sample of fumed silica was admixed with 5.0 ml of tri-n-butyltinchloride at 23° C. over a reaction time of 6 hours.

EXAMPLE IV

The same procedure as employed in Example I was followed to prepare a product of tri-n-butyltinacetate and fumed silica. A 16.6 g sample of fumed silica was admixed with 6.7 g of tri-n-butyltinacetate at 23° C. and reacted for 5 hours before collecting.

EXAMPLE V

The same general procedure as employed in Example II was followed to prepare a product of triphenyltinhydroxide and fumed silica. To 18.4 g of fumed silica was added a total of 8.4 g of triphenyltinhydroxide. For the first 3 hours the mixture was stirred at room temperature and then the temperature was raised to 150° C. for an additional 5 hours.

EXAMPLE VI

The same procedure as employed in Example I was followed to prepare a product of tributyltinhydride and fumed silica. To 20.1 g of fumed silica was admixed 7.0 ml of tributyltinhydride at 23° C. for 2.5 hours.

EXAMPLE VII

The same general procedure as employed in Example II was followed to prepare a product of tricyclohexyltinbromide and fumed silica. To 18.6 g of fumed silica was admixed a total of 5.0 g of tricyclohexyltinbromide. The mixing schedule was 1 hour at 23° C., 1 hour at 100° C. and finally 1 hour at 120° C.

EXAMPLE VIII

A product of triphenyltinchloride and fumed silica was prepared by the same general procedure of Example II. To 19.3 g of fumed silica was admixed 9.0 g of triphenyltinchloride for 1 hour at 23° C. and then 3 hours at 120° C.

Other compositions having varing concentrations of organotin groups with the maximum mmol of organotin per gram of silica dependent on the mmol of available free silanol sites on the silica surface are considered to be within the scope of this invention. That is, for example, when the silica compound is Cab-O-Sil ® M-5 (1.3 mmol of free silanol per gram of silica) a maximum of 1.3 mmol of organotin compound per gram of silica can be employed. The preferred stoichiometry between the free silanols on the silica surface and the organotin active sites is 1:1.

What is claimed is:

1. A biocidal composition comprising an organotin compound characterized by the structural formula $R_3SnX$ wherein R is an alkyl or aryl functionality and X is an anionic radical; and said organotin compound is covalently bonded to reactive silanol sites present on the surface of a silica compound to form a solid biocidal particle wherein the maximum mmol of said organotin compound is no more than the mmol of said silanol sites present on said silica surface.

2. The biocidal composition of claim 1 which additionally includes a carrier or film-forming vehicle containing said solid biocidal particle.

3. The biocidal composition of claim 2 where said carrier vehicle is a volatile or inert liquid.

4. The biocidal composition of claim 2 where said film-forming vehicle is a wax, paint, varnish or adhesive composition.

5. The biocidal composition of claim 1 where said organotin compound is tributyltinoxide.

6. The biocidal composition of claim 1 wherein said silica compound is fumed silica.

7. A method of protecting a surface from fouling organisms which comprises admixing in a carrier or film-forming vehicle a solid biocidal particle to form an admixture wherein said solid biocidal particle comprises an organotin compound characterized by the structural formula $R_3SnX$ wherein R is an alkyl or aryl functionality and X is an anionic radical; and said organotin compound is covalently bonded to reactive silanol sites present on the surface of a silica compound wherein the maximum mmol of said organotin compound is no more than the mmol of said silanol sites present on said silica surface, and treating said surface with said admixture.

8. The method of claim 7 where said carrier vehicle is a volatile or inert liquid.

9. The method of claim 7 where said film-forming vehicle is a wax, paint, varnish or adhesive composition.

10. The method of claim 7 where said organotin compound is tributyltinoxide.

11. The method of claim 7 wherein said silica compound is fumed silica.

* * * * *

UNITED STATES PATENT AND TRADEMARK OFFICE
CERTIFICATE OF CORRECTION

PATENT NO. : 4,543,127

DATED : September 24, 1985

INVENTOR(S) : Edward R. Falardeau

It is certified that error appears in the above-identified patent and that said Letters Patent is hereby corrected as shown below:

Cover page, right hand column, Attorney, Agent or Firm - "D. L. Conneglio" should read --D. L. Corneglio--.

Signed and Sealed this

Twenty-ninth Day of July 1986

[SEAL]

Attest:

DONALD J. QUIGG

Attesting Officer

Commissioner of Patents and Trademarks